United States Patent [19]
Oliver et al.

[11] Patent Number: 6,160,122
[45] Date of Patent: *Dec. 12, 2000

[54] PROCESS FOR THE PREPARATION OF A DISUBSTITUTED THIAZOLE

[75] Inventors: Patricia A. Oliver, Lindenhurst; Arthur J. Cooper, Lake Villa; John E. Lallaman, Beach Park; Denton C. Langridge, Wildwood; Jieh-Heh J. Tien, Libertyville, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/673,445

[22] Filed: Jun. 28, 1996

[51] Int. Cl.[7] .................................................. C07D 277/30
[52] U.S. Cl. ............................................................. 548/204
[58] Field of Search ............................................. 548/204

[56] References Cited

U.S. PATENT DOCUMENTS

| | | | |
|---|---|---|---|
| 4,810,799 | 3/1989 | Zanker | 548/226 |
| 5,597,928 | 1/1997 | Kempf | 548/204 |

FOREIGN PATENT DOCUMENTS

| | | | |
|---|---|---|---|
| 0687675 | 12/1995 | European Pat. Off. | 303/36 |
| 9414436 | 7/1994 | WIPO | 31/425 |

OTHER PUBLICATIONS

Mar., Advanced Organic Chemistry, 4th ed., pp. 419–424, 1992.

*Primary Examiner*—Robert Gerstl
*Attorney, Agent, or Firm*—Steven R. Crowley

[57] ABSTRACT

A process is disclosed for the preparation of N-((N-Methyl-N-((2-isopropyl-4-thiazolyl)methyl)amino)carbonyl)-amino acid derivatives.

20 Claims, No Drawings

PROCESS FOR THE PREPARATION OF A DISUBSTITUTED THIAZOLE

TECHNICAL FIELD

The present invention relates to a process for the preparation of N-((N-Methyl-N-((2-isopropyl-4-thiazolyl)methyl)amino)carbonyl)-amino acid derivatives or a salt thereof.

BACKGROUND OF THE INVENTION

It has recently been determined that HIV protease inhibiting compounds are useful for inhibiting HIV protease in vitro and in vivo and are also useful for inhibiting an HIV (human immunodeficiency virus) infection.

It has also recently been determined that compounds of the formula I:

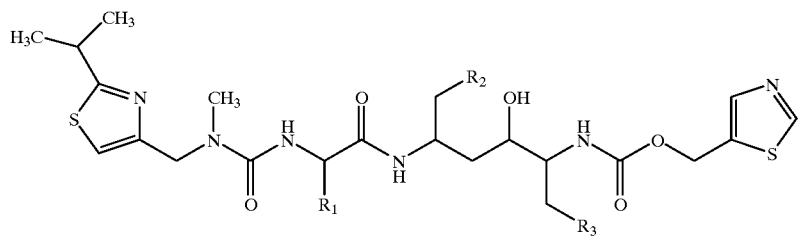

wherein $R_1$ is hydrogen, loweralkyl, alkoxyalkyl, hydroxyalkyl, cycloalkyl, cycloalkylalkyl, aryl and arylalkyl and $R_2$ and $R_3$ are phenyl are particularly useful as inhibitors of HIV protease and are useful for inhibiting HIV protease in vitro and in vivo and are also useful to inhibit HIV infections.

In particular, the compound of formula II has been found to be especially effective as an inhibitor of HIV-1 protease.

Particularly useful in the preparation of the compound of formula II and analogs thereof is a compound of formula III or a salt thereof, wherein R1 is defined as above.

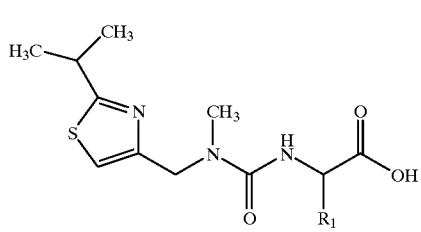

The preparation of compounds II and III and the use of compound II as an inhibitor of HIV protease are disclosed in PCT Patent Application No. WO94/14436, published Jul. 7, 1994, which is incorporated herein by reference. The method disclosed for preparing compound III (wherein $R_1$ is isopropyl) is shown in Scheme I. This method involves an urea bond forming coupling reaction of intermediates 1 and 2 in the presence of a catalyst such as 4-dimethylaminopyridine and the like to give ester 3. Ester hydrolysis of the valine carboxy protecting group (for example, lithium hydroxide hydrolysis) affords compound III. This process has the disadvantage of including the steps

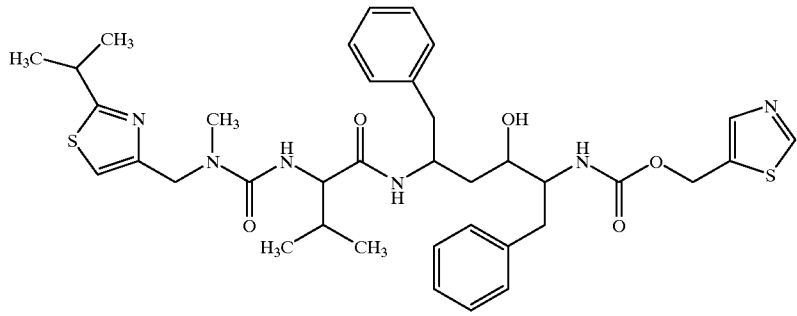

of carboxy protecting and then de-protecting the valine residue. A process that avoids protection and deprotection steps would be preferred. Therefore, there is a continuing need for an improved process for the preparation of III.

Scheme I

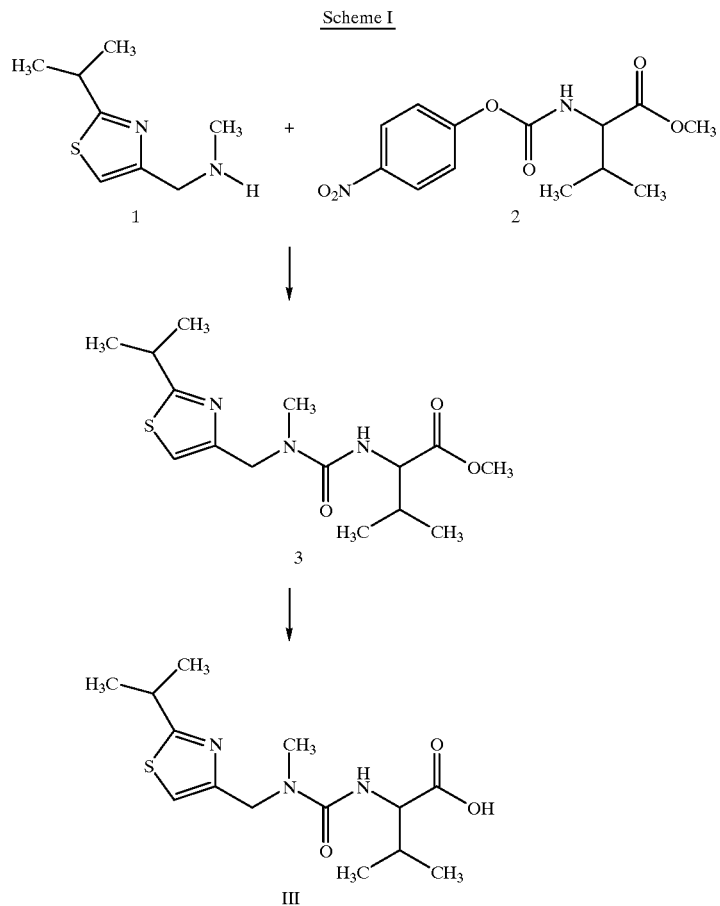

DISCLOSURE OF THE INVENTION

The present invention relates to a process for the preparation of N-((N-Methyl-N-((2-isopropyl-4-thiazolyl)methyl) amino)carbonyl)-amino acid derivatives or a salt thereof (compound III). The process comprises reacting 4 and 5 in the presence of a base derived from an alkali or alkaline earth metal cation or ammonium or a quarternary ammonium cation (see Scheme IIA). One variation on the process (see Scheme IIB) involves preforming salt 6 and preforming salt 7 and then reacting 6 with 7 to give 8 (compound III). Another variation on the process (see Scheme IIC) involves preforming salt 7 and then reacting 7 with amine 4. Yet another variation on the process (see Scheme IID) involves preforming salt 6 and then reacting 6 with carboxylic acid 5.

A preferred embodiment of the present invention relates to a process for the preparation of N-((N-Methyl-N-((2-isopropyl-4-thiazolyl)methyl)amino)-carbonyl)-L-valine or a salt thereof (compound III wherein $R_1$ is isopropyl).

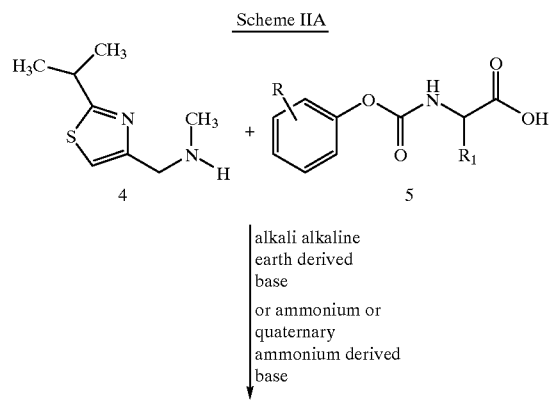

-continued

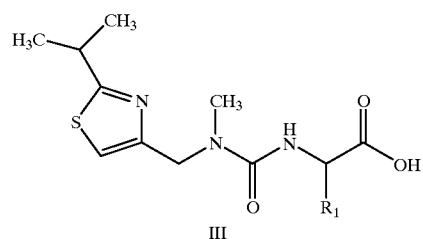

III

Scheme IIB

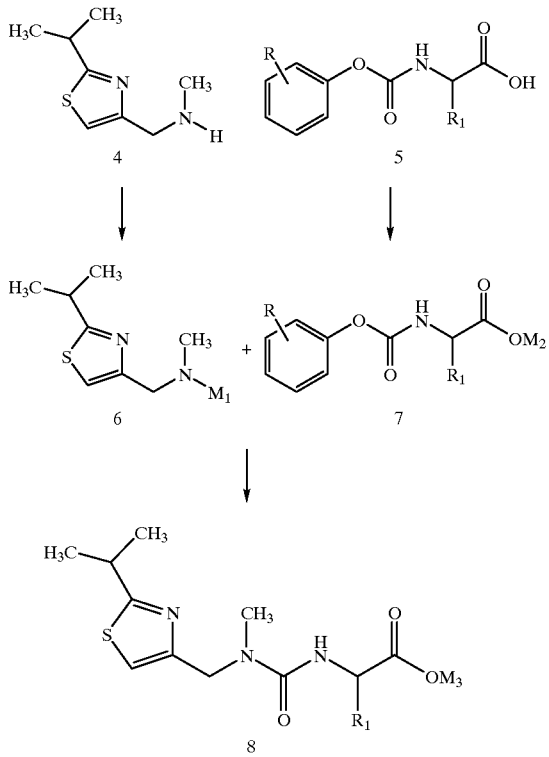

Scheme IIC

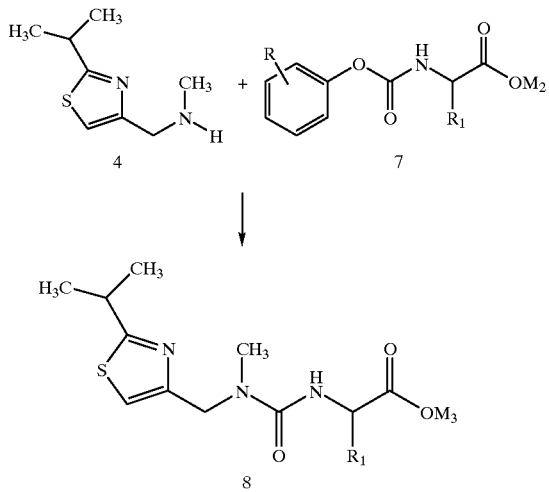

Scheme IID

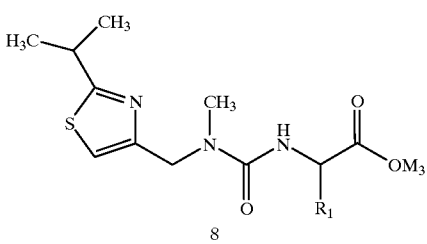

Typically, reactions involving compounds such as 5 result in the formation of the undesired carboxy anhydride by-product IV. This undesired by-product is minimized in the process of this invention.

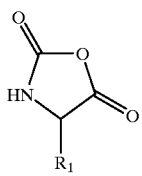

IV $M_1$ and $M_2$ are independently selected from cations based on the alkali or alkaline earth metals Li, Na, K, Rb, Cs, Fr, Be, Mg, Ca, Sr, Ba, or Ra, as well as ammonium and quaternary ammonium cations selected from the group consisting of ammonium, tetramethylammonium, tetraethylammonium and tetrabutylammonium. $M_3$ is selected from hydrogen and cations based on the alkali and alkaline earth metals Li, Na, K, Rb, Cs, Fr, Be, Mg, Ca, Sr, Ba, or Ra, as well as ammonium and quaternary ammonium cations selected from the group consisting of ammonium, tetramethylammonium, tetraethylammonium and tetrabutylammonium.

Representative bases which are useful in the process of the invention included sodium hydroxide (NaOH), lithium hydroxide (LiOH), potassium hydroxide (KOH), magnesium hydroxide $(Mg(OH)_2)$, barium hydroxide $(Ba(OH)_2)$, sodium hydride (NaH), lithium hydride (LiH), potassium hydride (KH), sodium phenoxide (NaOPh), lithium phenoxide (LiOPh), potassium phenoxide (KOPh), calcium hydride $(CaH_2)$ and the like. Hydrated bases, where possible, are also useful.

Preferred bases are sodium hydride, lithium hydride, lithium hydroxide, sodium hydroxide, sodium phenoxide or lithium phenoxide.

Most highly preferred bases are lithium hydroxide, lithium hydride or lithium phenoxide.

R is selected from hydrogen, loweralkyl, halo, haloalkyl, alkenyloxy, alkoxy, alkoxyalkoxy, alkoxycarbonyl, thioalkoxy, dialkylamino, nitro, carboxaldehyde and cyano. Preferred substituents R are hydrogen or nitro.

In the process of the invention, preferably, $M_1$ and $M_2$ are independently sodium or lithium, $M_3$ is hydrogen, sodium or lithium, R is hydrogen and $R_1$ is loweralkyl.

In the process of the invention, most preferably, $M_1$ and $M_2$ are independently sodium or lithium, $M_3$ is hydrogen, sodium or lithium, R is hydrogen and $R_1$ is isopropyl.

In the process of the invention, even more preferably, $M_1$ and $M_2$ are lithium, $M_3$ is hydrogen or lithium, R is hydrogen and $R_1$ is isopropyl.

In one embodiment, the process of this invention comprises reacting compound 5 with compound 4 (from about 1 molar equivalent to about 1.2 molar equivalents based on compound 5) in the presence of excess base (from about 1.05 to about 2.2 molar equivalents of base based on compound 5) in an inert solvent (for example, THF, methyl tert-butyl ether, or toluene and the like or a mixture of THF and water) at a temperature from about –20° C. to ambient temperature (25° C.).

In another embodiment, the process of this invention comprises reacting compound 6 with compound 7 (from about 1 molar equivalent to about 1.2 molar equivalents based on compound 6) in an inert solvent (for example, THF, methyl tert-butyl ether, or toluene and the like or a mixture of THF and water) at a temperature of from about –20° C. to ambient temperature (25° C.).

In this embodiment of the invention, salts 6 and 7 can be separately formed and then reacted together. For example, compound 4 can be reacted with from about 1.0 to about 1.2 molar equivalents (based on compound 4) of base (for example, sodium hydride, sodium phenoxide, lithium hydroxide, lithium hydride or lithium phenoxide and the like) in an inert solvent (for example, THF, methyl tert-butyl ether, or toluene and the like or a mixture of THF and water) at a temperature of from about –20° C. to ambient temperature (25° C.) to give compound 6. Compound 5 can be reacted with from about 1.0 to about 1.2 molar equivalents (based on compound 5) of base (for example, sodium hydride, sodium phenoxide, lithium hydroxide, lithium hydride or lithium phenoxide and the like) in an inert solvent (for example, THF, methyl tert-butyl ether, or toluene and the like or a mixture of THF and water) at a temperature of from about –20° C. to ambient temperature (25° C.) to give compound 7. Then solutions of 6 and 7 can be mixed at a temperature of from about –20° C. to ambient temperature (25° C.) to give compound 8.

In another embodiment of the invention, compound 4 (from about 0.8 to about 1.2 molar equivalents based on salt 7) can be added to a solution of salt 7 in an inert solvent (for example, THF, methyl tert-butyl ether, or toluene and the like or a mixture of THF and water) at a temperature of from about –20° C. to ambient temperature (25° C.), in the presence of excess base (from about 1.05 to about 2.0 molar equivalents of base based on salt 7) to give compound 8. Examples of bases include sodium hydride, sodium phenoxide, lithium hydroxide, lithium hydride or lithium phenoxide and the like.

In another embodiment of the invention, compound 5 can be added to a solution of salt 6 (from about 1.0 to about 1.2 molar equivalents based on compound 5) in an inert solvent (for example, THF, methyl tert-butyl ether, or toluene and the like or a mixture of THF and water) at a temperature of from about –20° C. to ambient temperature (25° C.), in the presence of excess base (from about 1.05 to about 2.0 molar equivalents of base based on compound 5) to give compound 8. Examples of bases include sodium hydride, sodium phenoxide, lithium hydroxide, lithium hydride or lithium phenoxide and the like.

In the process of this invention, the product can be isolated as the carboxylic acid (for example, by crystallization of the acid form) or as a carboxylate salt.

In the process of this invention, preferred bases are sodium hydride, sodium phenoxide, lithium hydroxide, lithium hydride or lithium phenoxide.

In the process of this invention, most preferred bases are lithium hydroxide, lithium hydride or lithium phenoxide.

In the process of this invention, preferred inert solvents are THF and mixtures of THF and water.

The term "alkali or alkaline earth metal" as used herein refers to those Group IA or Group IIA elements of the periodic table other than hydrogen. Examples of alkali or alkaline earth metals include Li, Na, K, Rb, Cs, Fr, Be, Mg, Ca, Sr, Ba, and Ra.

The term "ammonium or quaternary ammonium cations" as used herein refers to a nitrogen having four substituents and a positive charge. Examples of ammonium and quaternary ammonium cations include ammonium, tetramethylammonium, tetraethylammonium and tetrabutylammonium, as well as other examples described by S. M. Berge, et al., "Pharmaceutical Salts," *J. Pharm. Sci.*, 66 : 1–19 (1977) which is incorporated herein by reference.

The term "alkenyl" as used herein refers to a straight or branched chain hydrocarbon containing from 2 to 10 carbon atoms and also containing at least one carbon-carbon double bond. Examples of alkenylene include $CH_2=CH-$, $CH_3CH=CH-$, $-C(CH_3)=CH_2$, $CH_3CH=CHCH_2-$, and the like.

The term "alkenyloxy" as used herein refers to $R_5O-$ wherein $R_5$ is an alkenyl group.

The terms "alkoxy" and "thioalkoxy" as used herein refer to $R_6O-$ and $R_6S-$, respectively, wherein $R_6$ is a loweralkyl group.

The term "alkoxyalkoxy" as used herein refers to $R_7O-R_8O-$ wherein $R_7$ is loweralkyl as defined herein and $R_8$ is an alkylenyl group. Representative examples of alkoxyalkoxy groups include methoxymethoxy, ethoxymethoxy, t-butoxymethoxy and the like.

The term "alkoxyalkyl" as used herein refers to an alkoxy group appended to a loweralkyl radical.

The term "alkoxycarbonyl" as used herein refers to $R_9C(O)-$ wherein $R_9$ is an alkoxy group.

The term "alkylenyl" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "aryl" as used herein refers to a mono- or bicyclic carbocyclic ring system comprising 6 to 12 carbon atoms and having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, alkoxy, alkoxycarbonyl, thioalkoxy, dialkylamino, nitro, carboxaldehyde and cyano.

The term "arylalkyl" as used herein refers to an aryl group as previously defined, appended to a loweralkyl radical, for example, benzyl and the like.

The term "cycloalkyl" as used herein refers to an aliphatic ring system having 3 to 8 carbon atoms including, but not limited to, cyclopropyl, cyclopentyl, cyclohexyl, and the like.

The term "cycloalkylalkyl" as used herein refers to a cycloalkyl group appended to a loweralkyl radical, including but not limited to cyclohexylmethyl.

The term "dialkylamino" as used herein refers to —$NR_{10}R_{11}$ wherein $R_{10}$ and $R_{11}$ are independently selected from loweralkyl groups.

The term "halo" or "halogen" as used herein refers to —Cl, —Br, —I or —F.

The term "haloalkyl" as used herein refers to a loweralkyl group in which one or more hydrogen atoms are replaced by halogen, for example, chloromethyl, chloroethyl, trifluoromethyl and the like.

The term "hydroxyalkyl" as used herein refers to a loweralkyl radical to which is appended an hydroxy group.

The terms "loweralkyl" or "alkyl" as used herein refer to straight or branched chain alkyl radicals containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "salt" as used herein refers to an alkali or alkaline earth metal salt or an ammonium or quarternary ammonium salt of a carboxylic acid. Examples of alkali or alkaline earth metals include Li, Na, K, Rb, Cs, Fr, Be, Mg, Ca, Sr, Ba, and Ra.

The following examples will serve to further illustrate the processes of the invention. The following abbreviations are used: EtOAc for ethyl acetate, HOAc for acetic acid, MeOH for methanol, MTBE for methyl tert-butyl ether, and THF for tetrahydrofuran.

EXAMPLE 1

N-((N-Methyl-N-((2-isopropyl-4-thiazolyl)methyl) amino)carbonyl)-L-Valine

To a stirred slurry of 60% oil dispersion NaH (200 mg, 5 mmol) at <5° C. in 10 mL of THF was added N-phenoxycarbonyl-L-Valine (1.0 g, 4.2 mmol) followed by a 10 mL THF rinse and keeping the temperature <5° C. using an ice-water bath. In another flask, N-methyl-N-((2-isopropyl-4-thiazolyl)methyl)amine (851 mg, 5 mmol) was added to a <5° C. slurry of 60% oil dispersion NaH (220 mg, 5.5 mmol) in 10 mL of THF maintaining the temperature <5° C. Both solutions were stirred for 15 minutes, and then the acid salt solution was added to the amine salt solution in one portion. The reaction was allowed to proceed at <10° C. for 1 hour and then at ambient temperature for 30 minutes. The reaction was quenched by the addition of 10 mL of MeOH, and the reaction mixture was then concentrated in vacuo. The resulting residue was dissolved in a minimum of EtOAc and flash chromatographed on silica gel eluting with 1:1 ethyl acetate in isopropanol. The residue obtained was further purified by preparative thin layer chromatography eluting with 33.6% $CHCl_3$, 7.7% $H_2O$, 3.5% HOAc, 25.2% MeOH and 30% EtOAc to afford the title compound (310 mg, 24%) as a yellow oil.

EXAMPLE 2

Alternate Preparation of N-((N-Methyl-N-((2-isopropyl-4-thiazolyl)methyl)amino)carbonyl)-L-Valine To a stirred slurry of anhydrous 95% NaH (500 mg, 20.8 mmol) at −10° C. in 25 mL of THF was added N-phenoxycarbonyl-L-Valine (4.93 g, 20.8 mmol) followed by a 10 mL THF rinse keeping the temperature <0° C. using an ice-water bath. Following the addition of the N-protected Valine, N-methyl-N-((2-isopropyl-4-thiazolyl)methyl) amine (3.54 g, 20.8 mmol) was added at <0° C. The reaction was allowed to warm to ambient temperature. After 3 hours, 50 mL of THF was added followed by 25 mg (1 mmol) of NaH. After 16 hours at room temperature, the reaction was complete. The reaction was worked up by the procedures described in Example 1.

EXAMPLE 3

N-Phenoxycarbonyl-L-Valine Sodium Salt

To a solution of N-phenoxycarbonyl-L-Valine (5.00 g, 21.1 mmol) in 350 mL of toluene cooled to 0° C. in an ice bath was added dropwise a solution of sodium hydroxide (840 mg, 21 mmol) in 2 mL of distilled water. The reaction was stirred at 0° C. for 2 hours and then concentrated under reduced pressure. The residue was chased three time with toluene (150 mL) to afford the title compound as an oil (6.03 g).

EXAMPLE 4

Alternate Preparation of N-((N-Methyl-N-((2-isopropyl-4-thiazolyl)methyl)amino)carbonyl)-L-Valine To a stirred slurry of 95% NaH (355 mg, 14.1 mmol) at −5° C. in 15 mL of THF was added a solution of N-phenoxycarbonyl-L-Valine (2.99 g, 12.6 mmol) and N-methyl-N-((2-isopropyl-4-thiazolyl)methyl)amine (2.16 g, 12.7 mmol) in 15 mL of THF followed by a 5 mL THF rinse. The reaction mixture was stirred at or below 0° C. for three hours and then allowed to warm to ambient temperature. After two days at ambient temperature, the THF was removed under reduced pressure. The remaining aqueous residue was added to 31 mL of methyl tert-butyl ether and treated with stirring with a solution of 0.15 mL (1.8 mmol) of concentrated hydrochloric acid in 30 mL of water. The pH of the solution was adjusted to ~9 with 10% sodium hydroxide solution. The aqueous phase was washed with 30 mL of methyl tert-butyl ether. The aqueous phase was treated with 30 mL of toluene and acidified to pH 3 with 4 N HCl. The aqueous layer was separated and extracted with an additional 30 mL aliquot of toluene. The combined toluene extracts were concentrated under reduced pressure. The title compound was crystallized from toluene-heptane as a crystalline solid (3.32 g, 84%). m.p. 82.8–93.8° C. $^1$H NMR (CDCl$_3$, 400 MHz) δ 1.02 (d, 3H), 1.04 (d, 3H), 1.38 (d, 6H), 2.30 (m, 1H), 2.30 (m, 1H), 3.00 (s, 3H), 3.28 (m, 1H), 4.24 (dd, 1H), 4.48 (AB quartet, 2H), 6.10–6.14 (br s, 1H), 7.02 (s, 1H). $^{13}$C NMR (CDCl$_3$, 400 MHz) δ 18.1, 19.5, 23.0, 23.1, 29.9, 33.1, 34.9, 49.2, 59.6, 114.4, 149.4, 151.5, 159.8, 174.9. IR (film) 3200–3400, 1730,1620 cm$^{-1}$. High Resolution MS Calc for C$_{14}$H$_{23}$N$_3$SO$_3$: (FAB) m/e 314.1538 (M+H)$^+$. Found: 314.1530.

EXAMPLE 5

Alternate Preparation of N-((N-Methyl-N-((2-isopropyl-4-thiazolyl)methyl)amino)carbonyl)-L-Valine To a stirred slurry of 95% NaH (560 mg, 23.2 mmol) at −10° C. in 20 mL of THF was slowly added N-methyl-N-((2-isopropyl-4-thiazolyl)methyl)amine (3.76 g, 22.1 mmol) keeping the temperature not more than 0° C. THF (5 mL) was added as a rinse. A solution of N-phenoxycarbonyl-L-Valine (5.0 g, 21.1 mmol) dissolved in 20 mL of THF was added slowly keeping the temperature not more than 0° C. THF (5 mL) was added as a rinse. After 4 hours, water (100 mL) was added, and the THF was removed under reduced pressure. The pH was adjusted to 9 with concentrated HCl, and the phenol by-product was removed with methyl tert-butyl ether washes (3×60 mL). The aqueous phase was stirred with 70 mL of toluene and adjusted to pH 3 with 4 N HCl. The aqueous phase was separated and extracted twice more with toluene (2×70 mL). The combined toluene extracts were concentrated under reduced pressure, and the residue was redissolved in toluene and heptane (50 mLs of a 1:1 v/v solution), warmed to 50° C. and allowed to cool to ambient temperature. The product was collected by filtration, washed with heptane and dried under vacuum to afford the title compound as a white powder in 83% yield.

EXAMPLE 6

Alternate Preparation of N-((N-Methyl-N-((2-isopropyl-4-thiazolyl)methyl)amino)carbonyl)-L-Valine To lithium hydroxide monohydrate (1.06 g, 25.2 mmol) slurried in 20 mL of THF and cooled to less than 5° C. in an ice bath was added N-methyl-N-((2-isopropyl-4-thiazolyl) methyl)amine (3.78 g, 22.2 mmol) followed by a 5 mL THF rinse. A solution of N-phenoxycarbonyl-L-Valine (5.0 g, 21.1 mmol) in 20 mL of THF was added followed by a 5 mL THF rinse. Water (1.04 mL) was added, the cooling bath was removed, and the reaction was stirred at ambient temperature for 4.5 hours. Water (55 mL) was added, and the THF was removed under reduced pressure. Methyl tert-butyl ether (50 mL) was added, and as the solution stirred, the pH was adjusted to 9 with 4 N HCl. The aqueous phase was separated and washed with another 50 mL portion of MTBE. The aqueous product layer was stirred with 50 mL of toluene and adjusted to pH 3 with 4 N HCl. The aqueous layer was separated and extracted once more with toluene (50 mL). The combined toluene extracts were concentrated under reduced pressure. The residue obtained was redissolved in toluene, filtered, and rinsed with toluene. The combined filtrates were concentrated under reduced pressure. The product was crystallized from toluene-heptane (50 mLs of a 1:1 v/v solution), washed with heptane, and dried under vacuum to afford the title compound as a white powder.

EXAMPLE 7

Alternate Preparation of N-((N-Methyl-N-((2-isopropyl-4-thiazolyl)methyl)amino)carbonyl)-L-Valine To a solution of phenol (2.18 g, 23.2 mmol) in THF (25 mL) was added 50% NaOH solution (1.86 g, 23.2 mmol) at ambient temperature. After the exotherm subsided, N-methyl-N-((2-isopropyl-4-thiazolyl)methyl)amine (3.95 g, 23.2 mmol) was added. The solution was cooled to 15° C., and then a solution of N-phenoxycarbonyl-L-Valine (5.0 g, 21.1 mmol) dissolved in 25 mL of THF was added slowly. An ice bath was used to maintain the temperature between 15 and 20° C. Following a 5 mL THF rinse, the reaction was allowed to warm to ambient temperature. After three hours, an additional aliquot of 50% NaOH solution (90 mg, 2.3 mmol) was added. After 19 hours, the reaction was quenched by the addition of 100 mL of water and the THF removed under reduced pressure. The remaining aqueous phase was washed with MTBE (3×60 mL), toluene (70 mL) was added, and the pH was adjusted to 3.7 with 4 N HCl. The layers were separated, and the aqueous phase was extracted with two additional aliquots (70 mL) of toluene. The combined toluene extracts were concentrated in vacuo. The resulting oil was crystallized using toluene and heptane to give the title compound (5.1 g, 78%).

EXAMPLE 8

Alternate Preparation of N-((N-Methyl-N-((2-isopropyl-4-thiazolyl)methyl)amino)carbonyl)-L-Valine To a solution of LiOH monohydrate (970 mg, 23.2 mmol) and phenol (2.18 g, 23.2 mmol) dissolved in 25 mL of THF and cooled with an ice bath to 3–6° C. was added N-methyl-N-((2-isopropyl-4-thiazolyl)methyl)amine (3.95 g, 23.2 mmol) followed by a 1 mL THF rinse. To this mixture was slowly added a solution of N-phenoxycarbonyl-L-Valine (5.0 g, 21.1 mmol) dissolved in 20 mL of THF maintaining the temperature between 3° C. and 8° C. Following the addition and a 5 mL THF rinse, the cooling bath was removed, and the reaction was allowed to warm to ambient temperature. After stirring for 3 hours at ambient temperature, an additional aliquot of LiOH monohydrate (440 mg, 10.4 mmol) was added. One hour later, the reaction was treated with 100 mL of water and the THF removed under reduced pressure. The aqueous phase was adjusted to pH 9 using concentrated HCl and then washed with MTBE (3×60 mL). Toluene (60 mL) was added to the aqueous phase which was then acidified to pH 2.5 using 4 N HCl. The toluene phase was separated, and the aqueous phase was back extracted with four 60 mL aliquots of toluene. The combined organic extracts were concentrated under reduced pressure. The oil obtained was crystallized from toluene-heptane to give the title compound (5.41 g, 82%).

EXAMPLE 9

N-((N-Methyl-N-((2-isopropyl-4-thiazolyl)methyl)amino)carbonyl)-L-Valine Lithium salt To a suspension of LiOH monohydrate (970 mg, 23.2 mmol) in 55 mL of THF cooled in an ice bath to 3–6° C. was added N-methyl-N-((2-isopropyl-4-thiazolyl)methyl)amine (3.95 g, 23.2 mmol) followed by a 1 mL THF rinse. To this mixture was slowly added a solution of N-phenoxycarbonyl-L-Valine (5.0 g, 21.1 mmol) dissolved in 20 mL of THF maintaining the temperature between 3° C. and 8° C. Following the addition, a 4 mL THF rinse and the addition of 6 mL of water, the cooling bath was removed, and the reaction was allowed to warm to ambient temperature. After 90 minutes at ambient temperature, an additional aliquot of LiOH monohydrate (270 mg, 6.3 mmol) was added. When the reaction was complete, the product was collected by filtration and washed with 10:1 heptane-THF to afford 5.53 g (78%) of the title compound. $^{13}$C NMR (CDCl$_3$, 400 MHz) δ 18.5, 19.8, 23.2, 30.3, 33.1, 34.6, 48.6, 114.0, 115.6, 129.3, 159.2, 178.5. IR (film) 3200–3700, 1600, 1530 cm$^{-1}$. MS Calc for $C_{14}H_{22}N_3SO_3Li$: (FAB+) m/e 320 (M+H)$^+$, (FAB−) m/e 312.

EXAMPLE 10

Alternate Preparation of N-((N-Methyl-N-((2-isopropyl-4-thiazolyl)methyl)amino)carbonyl)-L-Valine To a suspension of LiOH monohydrate (3.2 kg, 76.54 mol) in THF (66 kg) at 0° C. to 6° C. was added 11.3 kg (66.4 mol) of N-methyl-N-((2-isopropyl-4-thiazolyl)methyl)amine, followed by a 15 kg THF rinse. To this solution was added a cooled (0° C. to 6° C.) solution of N-phenoxycarbonyl-L-Valine (15 kg, 63.22 mol) dissolved in 41 kg of THF. Following a 25 kg THF rinse, 3.5 kg of water was added, and the reaction mixture was allowed to warm to 20° C. After 3 hours, the reaction was cooled to 10° C. and quenched with water (180 kg). The THF was removed under reduced pressure, MTBE (111 kg) was added, and the biphasic solution was adjusted to pH 9.0 with 4 N HCl. The layers were separated and the aqueous layer was washed with an additional 111 kg of MTBE. The aqueous layer was stirred with 130 kg of toluene and adjusted to pH 3 with 4 N HCl, and the phases were separated. The aqueous layer was back-extracted once more with 130 kg of toluene. The combined organic extracts were filtered and the material removed by filtration washed with toluene (50 kg). The combined filtrates were concentrated in vacuo. The residue obtained was redissolved in 100 kg of toluene and re-concentrated in vacuo. The residue obtained was cystallized using toluene and heptane to afford 16.6 kg (83.8%) of the title compound.

EXAMPLE 11

Alternate Preparation of N-((N-Methyl-N-((2-isopropyl-4-thiazolyl)methyl)amino)carbonyl)-L-Valine To a suspension of LiOH monohydrate (1.06 g, 25.2 mmol) in THF (20 mL) at 0° C. to 5° C. was added 3.78 g (22.2 mmol) of N-methyl-N-((2-isopropyl-4-thiazolyl)methyl)amine, followed by a 5 mL THF rinse. To this solution was added a solution of N-phenoxycarbonyl-L-Valine (5.0 g, 21.1 mmol) in 20 mL of THF. Following a 5 mL THF rinse, 0.5 mL of water was added, and the reaction mixture was allowed to warm to 20° C. with stirring. After 6 hours, the reaction was cooled to 10° C. and quenched with water (55 mL). The THF was removed under reduced pressure, MTBE (50 mL) was added, and the biphasic solution was adjusted to pH 9.0 with 4 N HCl. The layers were separated and the aqueous layer was washed with an additional 50 mL of MTBE. The aqueous layer was stirred with 130 mL of toluene and adjusted to pH 3 with 4 N HCl, and the phases were separated. The aqueous, product-containing layer was stirred with 50 mL of toluene and adjusted to pH=3.0 with 4 N HCl. The aqueous layer was separated and extracted once more with 50 mL of toluene. The combined organic extracts were concentrated in vacuo. The residue obtained was redissolved in toluene, filtered and rinsed with toluene (approx. 50 mL total). The combined filtrates were concentrated in vacuo to an oil. Toluene (25 mL) and heptane (25 mL) were aded and warmed to 50° C. The clear solution was allowed to cool until cloudy and then was seeded with N-((N-Methyl-N-((2-isopropyl-4-thiazolyl)methyl)amino)carbonyl)-L-Valine. The resulting slurry was stirred for at least 12 hours and the product was collected by filtration and washed with heptane (5 mL). The resulting solid was dried in a vacuum oven at 50° C. to yield the desired product as a white powder.

EXAMPLE 12

Alternate Preparation of N-((N-Methyl-N-((2-isopropyl-4-thiazolyl)methyl)amino)carbonyl)-L-Valine To a suspension of calcium hydride (o.98 g, 23.2 mmol) in THF (25 mL) at 0° C. to 5° C. was added 3.94 g (23.1 mmol) of N-methyl-N-((2-isopropyl-4-thiazolyl)methyl)amine. To this was added a solution of N-phenoxycarbonyl-L-Valine (5.0 g, 21.1 mmol) in 20 mL of THF. Following a 5 mL THF rinse, 4.0 mL of water was added, and the reaction mixture was allowed to warm to 20° C. with stirring. After 2 hours, HPLC analysis (t=12.6 min; HPLC conditions: 65% 0.03M KH2PO4 buffer/35% acetonitrile; pH=4; 5μ nucleosil; 4.6×250 mm; 1 mL/min; 205 nm) indicated that the reaction was complete and the desired product had been formed.

EXAMPLE 13

N-phenoxycarbonyl-L-Valine

Into a reactor equipped with an overhead stirrer, chiller, pH probe and thermocouple was added lithium chloride (15.6 kg, 368 moles), L-valine (26.0 kg, 222 moles), neutral alumina (8.1 kg, 150 mesh, Aldrich) and 156 kg of distilled water. The heterogeneous mixture was stirred and cooled to −14° C.±5° C. The pH was adjusted to 10.1 with 10% aqueous lithium hydroxide. Precooled (−20° C.) phenylchlorformate (36.6 kg, 234 moles) was added while maintaining a temperature of not more than −9° C. and the pH was controlled during the reaction (maintaining a pH within the range of 9.5 to 10.5 with a target of 10.0) using a continuous addition of 10% aqueous lithium hydroxide.

The reaction was stirred for 2 hours at about −14° C. The reaction mixture was filtered through Celite and the filter cake was washed with 42 kg of distilled water. The aqueous filtrate was extracted with methyl t-butyl ether (65 kg) to remove residual phenol. The aqueous phase was then cooled to 0–5° C. and mixed with 200 kg of toluene. The stirred biphasic solution was adjusted to pH 1.8–2.0 with 25% (w/w) sulfuric acid. The toluene layer was concentrated at not more than 40° C. to approximately 120 L, filtered (30 kg rinse of toluene) and then concentrated again at not more than 40° C. to approximately 120 L.

To the resulting solution was added 44.2 kg of heptane and the resulting solution was heated to 40° C.±10° C. for 15 minutes. The heat was removed and the solution was seeded and stirred overnight. The product crystallized on the walls of the reactor and was resuspended in 80 kg of toluene, reconcentrated at not more than 50° C. to approximately 130 L, then 45.2 kg of heptane was added. The resulting solution was then heated to 40° C.±10° C. for not less than 15 minutes and then cooled at not more than 20° C./hour to 18° C.±5° C. After not less than 12 hours, the resulting white slurry was cooled to 14° C.±5° C. and stirred for not less than 3 hours. The white slurry was filtered and the solid washed with 41 kg of 1:1 toluene/heptane. The solid product was dried at not more than 50° C. to provide the desired product (47.8 kg) as a white powder. m.p. 84.5–85.5° C. IR 1690 cm$^{-1}$ (C=O), 1718 cm$^{-1}$ (C=O).

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of a compound of the formula:

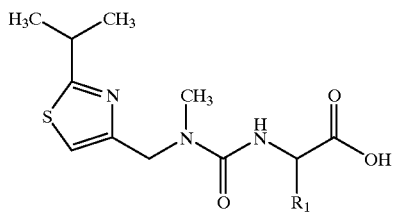

wherein $R_1$ is hydrogen, loweralkyl, alkoxyalkyl, hydroxyalkyl, cycloalkyl, cycloalkylalkyl, aryl or arylalkyl, or a salt thereof comprising reacting N-methyl-N-((2-isopropyl-4-thiazolyl)methyl)amine with a compound of the formula:

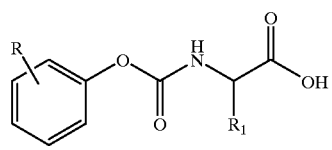

wherein R is selected from the group consisting of hydrogen, loweralkyl, halo, haloalkyl, alkenyloxy, alkoxy, alkoxyalkoxy, alkoxycarbonyl, thioalkoxy, dialkylamino, nitro, carboxaldehyde and cyano and $R_1$ is defined as above, in the presence of a base selected from the group consisting of sodium hydride, lithium hydride, sodium hydroxide, lithium hydroxide, sodium phenoxide and lithium phenoxide.

2. The process of claim 1 wherein the base is selected from the group consisting of sodium hydride, sodium phenoxide, lithium hydroxide and lithium phenoxide.

3. The process of claim 1 wherein the base is lithium hydroxide.

4. The process of claim 1 wherein R is H and $R_1$ is loweralkyl.

5. A process for the preparation of N-((N-Methyl-N-((2-isopropyl-4-thiazolyl)methyl)amino)carbonyl)-L-Valine or a salt thereof comprising reacting N-methyl-N-((2-isopropyl-4-thiazolyl)methyl)amine with a compound of the formula:

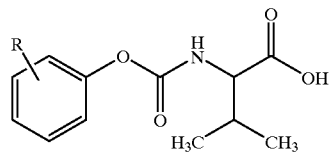

wherein R is selected from the group consisting of hydrogen, loweralkyl, halo, haloalkyl, alkenyloxy, alkoxy, alkoxyalkoxy, alkoxycarbonyl, thioalkoxy, dialkylamino, nitro, carboxaldehyde and cyano, in the presence of a base selected from the group consisting of sodium hydride, lithium hydride, sodium hydroxide, lithium hydroxide, sodium phenoxide and lithium phenoxide.

6. The process of claim 5 wherein the base is selected from the group consisting of sodium hydride, sodium phenoxide, lithium hydroxide and lithium phenoxide.

7. The process of claim 5 wherein the base is lithium hydroxide.

8. The process of claim 5 comprising reacting N-phenoxycarbonyl-L-Valine with N-methyl-N-((2-isopropyl-4-thiazolyl)methyl)amine in the presence of from about 1.05 to about 2.2 molar equivalents of a base (based on N-phenoxycarbonyl-L-Valine) selected from the group consisting of sodium hydride, lithium hydride, sodium hydroxide, lithium hydroxide, sodium phenoxide and lithium phenoxide.

9. The process of claim 8 wherein the base is lithium hydroxide.

10. The process of claim 5 comprising (a) converting the compound of the formula:

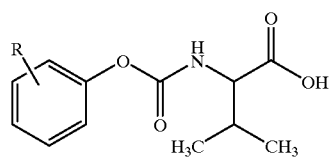

wherein R is selected from the group consisting of hydrogen, loweralkyl, halo, haloalkyl, alkenyloxy, alkoxy, alkoxyalkoxy, alkoxycarbonyl, thioalkoxy, dialkylamino, nitro, carboxaldehyde and cyano to a salt of the formula:

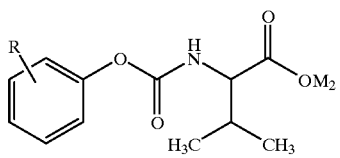

wherein R is defined as above and $M_2$ is Li or Na;

(b) converting N-methyl-N-((2-isopropyl-4-thiazolyl)methyl)amine to a salt of the formula:

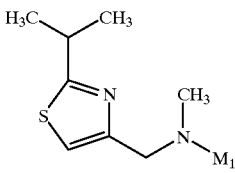

wherein $M_1$ is Li or Na; and (c) reacting the salts resulting from steps (a) and (b).

11. The process of claim 10 wherein $M_1$ is Li or Na, $M_2$ is Li or Na and R is H.

12. The process of claim 10 wherein $M_1$ is Li, $M_2$ is Li and R is H.

13. The process of claim 5 comprising reacting a compound of the formula:

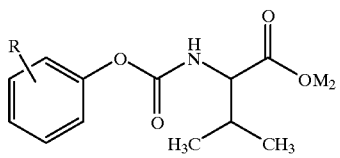

wherein R is selected from the group consisting of hydrogen, loweralkyl, halo, haloalkyl, alkenyloxy, alkoxy, alkoxyalkoxy, alkoxycarbonyl, thioalkoxy, dialkylamino, nitro, carboxaldehyde and cyano and $M_2$ is Li or Na with N-methyl-N-((2-isopropyl-4-thiazolyl)methyl)amine in the presence of excess base.

14. The process of claim 13 wherein $M_2$ is Li or Na and R is H.

15. The process of claim 13 wherein $M_2$ is Li and R is H.

16. The process of claim 5 comprising reacting a compound of the formula:

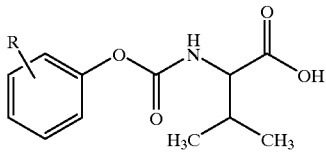

wherein R is selected from the group consisting of hydrogen, loweralkyl, halo, haloalkyl, alkenyloxy, alkoxy, alkoxyalkoxy, alkoxycarbonyl, thioalkoxy, dialkylamino, nitro, carboxaldehyde and cyano with a compound of the formula:

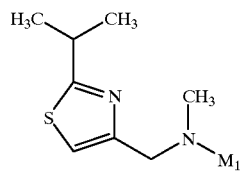

wherein $M_1$ is Li or Na in the presence of excess base.

17. The process of claim 16 wherein $M_1$ is Li or Na and R is H.

18. The process of claim 16 wherein $M_1$ is Li and R is H.

19. A process for the preparation of N-((N-Methyl-N-((2-isopropyl-4-thiazolyl)methyl)amino)carbonyl)-L-Valine or a salt thereof comprising reacting N-methyl-N-((2-isopropyl-4-thiazolyl)methyl)amine with N-phenoxycarbonyl-L-Valine in the presence of about 1.2 molar equivalents (based on N-phenoxycarbonyl-L-Valine) of a base selected from the group consisting of lithium hydroxide and lithium phenoxide in a solvent comprising a mixture of THF and water.

20. The process of claim 19 wherein the base is LiOH monohydrate.

* * * * *